(12) United States Patent
Thierman

(10) Patent No.: US 6,790,184 B2
(45) Date of Patent: Sep. 14, 2004

(54) DEVICE FOR MEDICAL PERCUSSION

(75) Inventor: Jonathan S. Thierman, Boston, MA (US)

(73) Assignee: Sure-Shot Medical Device, Inc., Reno, NV (US)

( * ) Notice: Subject to any disclaimer, the term of this patent is extended or adjusted under 35 U.S.C. 154(b) by 215 days.

(21) Appl. No.: 10/235,680

(22) Filed: Sep. 5, 2002

(65) Prior Publication Data
US 2004/0059246 A1 Mar. 25, 2004

(51) Int. Cl.[7] .............................................. A61B 19/00
(52) U.S. Cl. ....................................................... 600/553
(58) Field of Search ................................. 600/553, 528, 600/552; 181/131, 126; 381/67; D24/134, 142; 606/238

(56) References Cited

U.S. PATENT DOCUMENTS

| 599,064 | A | 2/1898 | Papendell |
| 989,714 | A | 4/1911 | Lepre |
| 1,812,619 | A | 6/1931 | Blattner et al. |
| 2,261,375 | A | 11/1941 | Jacobs |
| 4,116,235 | A | * 9/1978 | Fuhr et al. ................. 606/238 |
| 4,302,627 | A | 11/1981 | Inoue |
| D274,554 | S | 7/1984 | Duffy |
| 4,669,454 | A | 6/1987 | Shamos |
| 5,003,605 | A | 3/1991 | Phillipps et al. |
| 5,183,003 | A | 2/1993 | Powell et al. |
| 5,662,686 | A | 9/1997 | Newsum |
| 5,686,652 | A | 11/1997 | Pfund |
| 5,931,792 | A | 8/1999 | Packard et al. |
| 5,960,089 | A | 9/1999 | Bouricius et al. |
| 6,228,042 | B1 | 5/2001 | Dungan |
| D449,108 | S | 10/2001 | Najmi |
| 6,485,434 | B1 | * 11/2002 | Kahana et al. ............. 600/552 |
| 6,510,918 | B2 | * 1/2003 | Bates ......................... 181/131 |

* cited by examiner

Primary Examiner—Eric F. Winakur
Assistant Examiner—Brian Szmal
(74) Attorney, Agent, or Firm—Hamilton, Brook, Smith & Reynolds P.C.

(57) ABSTRACT

A mechanical tapper clips onto the end of a stethoscope. The device is operated by pressing a small plunger with the index finger of the hand holding the end of the stethoscope onto the patient's body to aid the percussion portion of a physical exam.

17 Claims, 7 Drawing Sheets

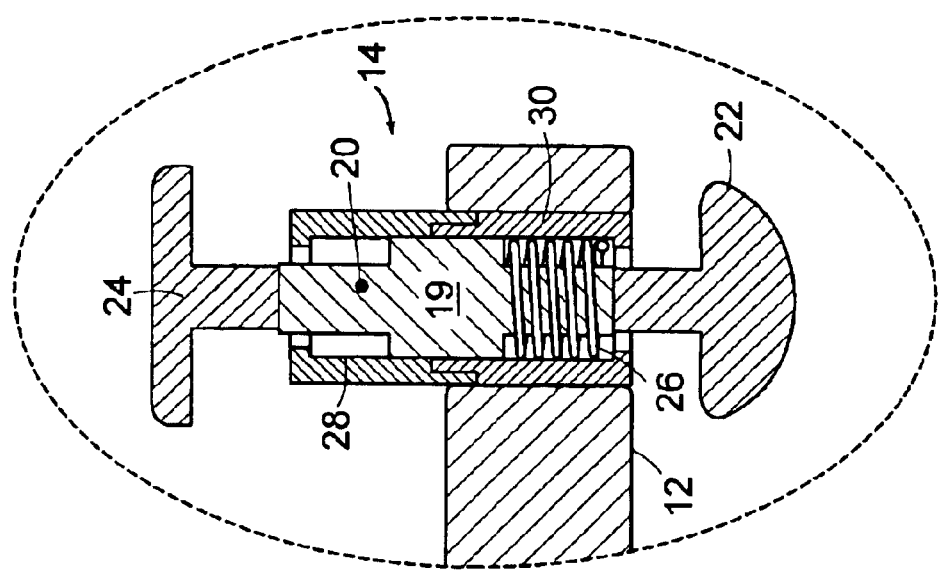
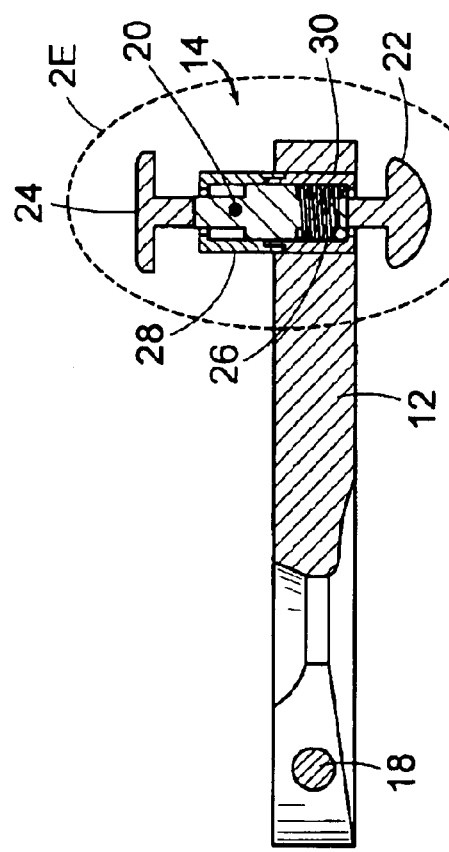
FIG. 2E
FIG. 2A

DEVICE FOR MEDICAL PERCUSSION

BACKGROUND

The percussion examination is an integral portion of every general physical exam of the thorax and many specialty exams including the pulmonary exam and the abdominal exam. The percussion exam is used to identify a variety of normal anatomical landmarks and to identify pathological conditions such as ascites, pulmonary infiltrates, and organomegally. The standard percussion exam is performed by placing one hand with spread fingers on the patient. One finger of the other hand is used to strike one finger of the hand on the patient in a brisk swinging motion. The resulting tapping action results in an audible sound which may be characterized as "tympanic", "resonant", "dull", or a variety of other variations. These sounds are then used to identify the boundaries of organs or the presence of abnormalities.

The sound heard from the standard method of percussion is often very faint and therefore very difficult to interpret. In addition to being difficult to hear, the quality may be affected by the characteristics of the examiner's fingers themselves and the examiner's personal exam technique. The standard exam consists of multiple taps on the patient used for point to point comparison of the changes in sound at different places on the patient. Therefore, variations in the technique from one tap to another or one physician to another may affect the results of the exam.

SUMMARY

A small device clips onto the end of a stethoscope and aids during the percussion portion of a physical exam of the thorax or abdomen. The device is essentially a small mechanical "tapper" which is operated by pressing a small plunger with the index finger of the hand holding the end of the stethoscope onto the patient's body. During a normal percussion exam, the physician taps on the abdomen or thorax with a finger from one hand hitting a finger of the other hand placed on the body. The very faint sounds heard from this action can be classified as "tympanic, dull, resonant, etc" and help to diagnose organomegaly, ascities, lung infiltrates and other anatomy and abnormalities. This device aids in the exam by amplifying the percussion sounds heard because it is used together with the stethoscope. It also allows for one hand operation so this exam can be easily combined with the auscultation portion of the regular physical exam.

In some embodiments, the device includes a base adapted to be clipped to the head of the stethoscope with a hammer support extending over a patient, and a hammer supported by the hammer support and actuated by a user to tap on the patient. The hammer may include a finger pad that is depressed by the user to actuate the hammer, and a flared piston head piece that taps on the patient when the user depresses the finger pad. The finger pad and the head piece can be made from stainless steel. In certain embodiments, the hammer includes a main piston body positioned within a casing that is supported by the hammer support. The casing may be made from stainless steel, while the piston body may be made from brass.

Some embodiments can have a spring positioned around at least a portion of the main piston body and within the casing. In such embodiments, the spring acts to return the hammer to its starting position after being actuated by the user. The spring can be a stainless steel compression spring. The base can be secured to the head of the stethoscope with a set-screw.

Some embodiments may have one or more of the following advantages. The device greatly improves acoustics due to its design and use in conjunction with the stethoscope. In addition, the device allows for a one-hand percussion examination which will allow the healthcare professional to use the other hand for other purposes and to access portions of the body which may be more difficult to reach with two hands. This device conveniently attaches to the stethoscope and therefore is easy to carry and use. The spring-loaded piston provides a regular tapping action and may allow for a more astute diagnose of differences in the acoustic response from one point to another on the patient.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2A is a cross-sectional view of the medical percussion device along the line 2A—2A of FIG. 2;

FIG. 2E is a close-up view of the medical percussion device in the region 2E of FIG. 2A;

DETAILED DESCRIPTION OF THE INVENTION

Figure 1:
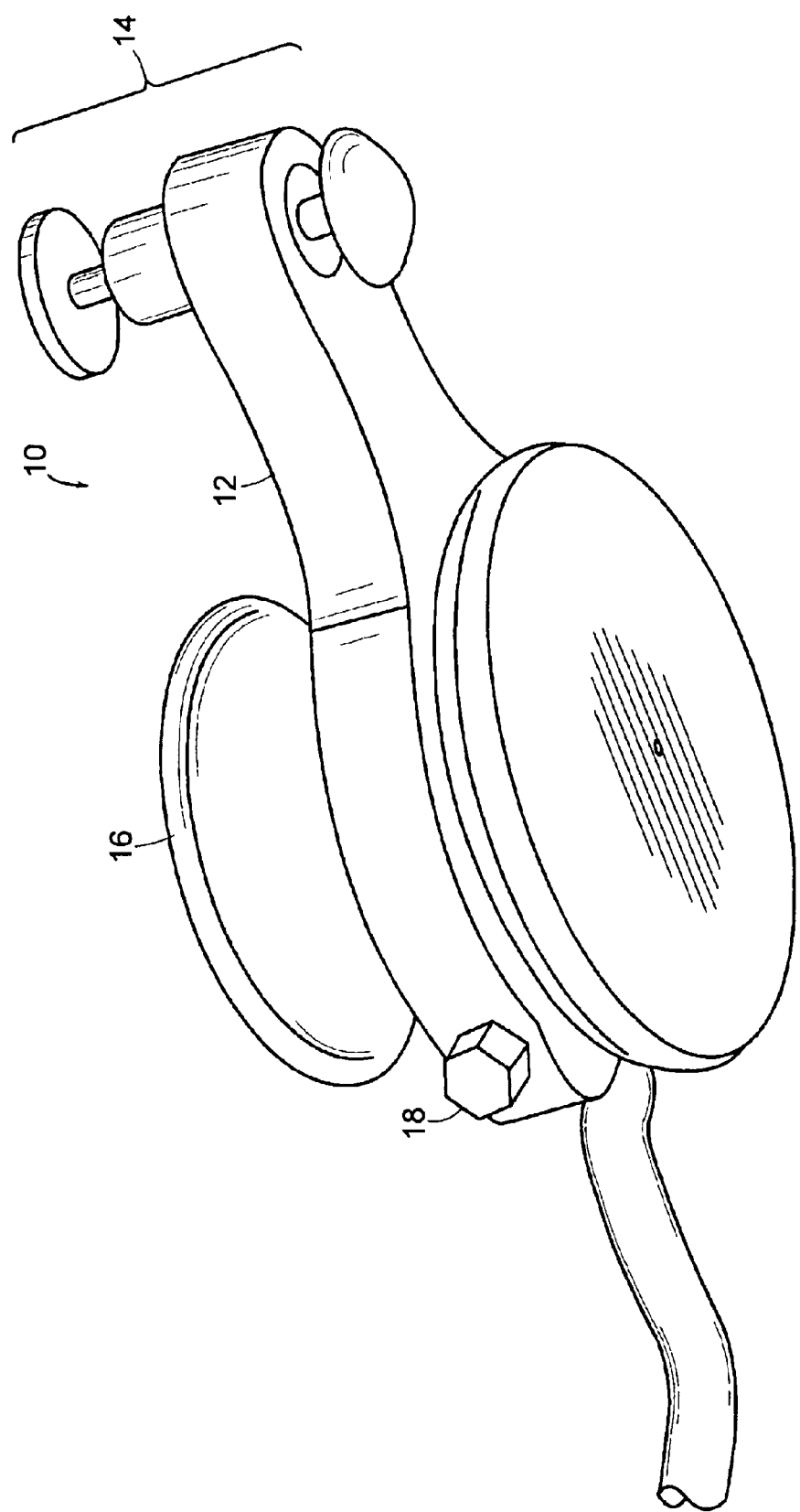
FIG. 1 is a perspective view of a stethoscope head with a medical percussion device in accordance with the invention.
Figure 1A:
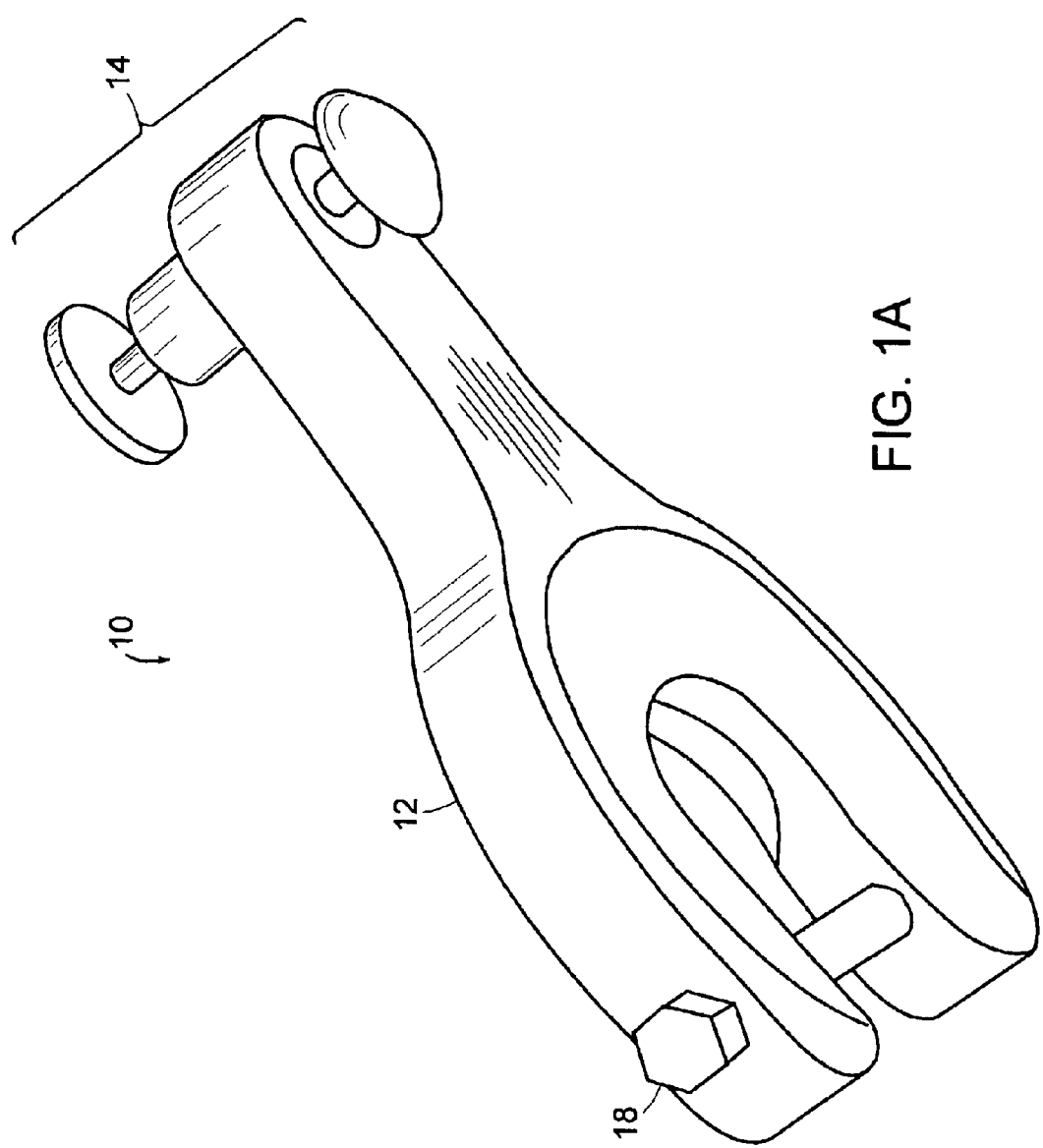
FIG. 1A is a perspective view of the medical percussion device of FIG. 1.
Figure 2:
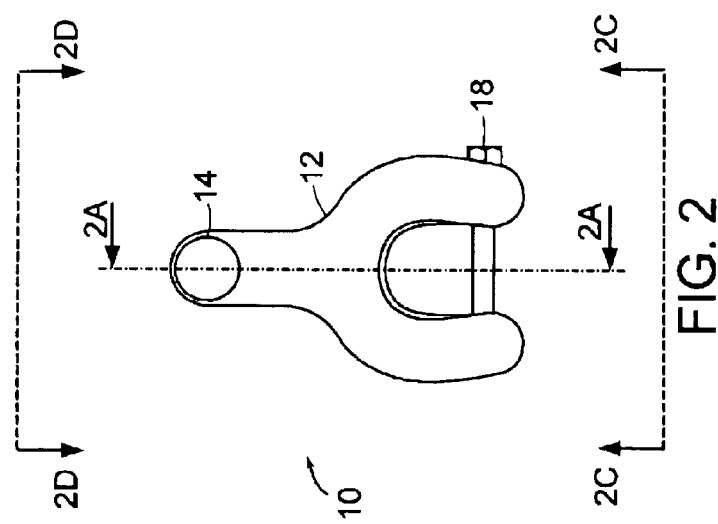
FIG. 2 is a top view of the medical percussion device of FIGS. 1 and 1A.
Figure 2B:
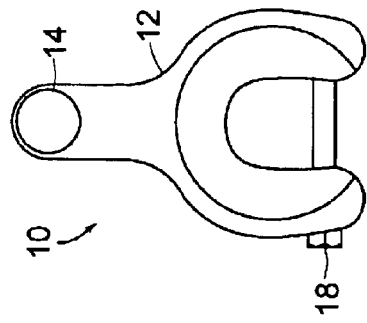
FIG. 2B is a bottom view of the medical percussion device of FIGS. 1 and 1A.
Figure 2C:
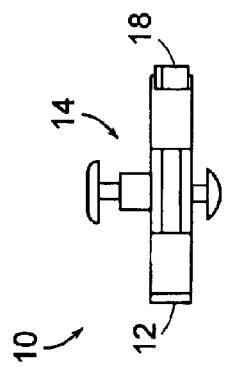
FIG. 2C is an end view of the medical percussion device along the line 2C—2C of FIG. 2.
Figure 2D:
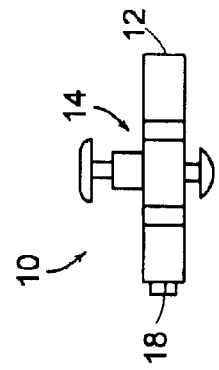
FIG. 2D is an end view of the medical percussion device along the line 2D—2D of FIG. 2.

A description of preferred embodiments of the invention follows.

Referring to FIGS. 1, 1A, and 2–2D, there is shown a medical percussion device 10, which is a ring-shaped device approximately 2 inches in diameter constructed from either metal or plastic. It has two aspects to its design: a base portion 12 and a hammer-action assembly 14.

The base portion 12 is designed to attach to a stethoscope 16 (FIG. 1) and is shaped like an open-ended ring so that it can slip around the head of the stethoscope. The base 12 includes a screw clamp, such as a set-screw 18, to help hold the percussion device 10 securely in place on the stethoscope head 16.

The base portion 12 is made from surgical grade stainless steel and is machined from one solid piece of metal. The base portion 12 has two smaller holes (one is threaded) on the two "tails" so that the stainless steel thumb screw 18 can be fed through this part in order to secure the base 12 to the stethoscope-head 16. The other side of the base piece 12 has a wide threaded hole to accommodate the hammer-action assembly 14 described below. The hammer-action assembly 14 screws into the base 12 at this larger hole.

Referring now to FIG. 2E, the hammer-action assembly 14 includes a piston assembly 19 having a metal piston 20 with detachable (screw in) flared head 22 and a detachable (screw in) finger pad 24, a spring 26, and a casing tube made from two parts 28 and 30. The flared head 22 of the piston comes into contact with the patient's skin as the piston is pressed by an examining medical professional. The finger pad 24 is the portion of the hammer-action assembly 14 that is depressed by the physician during the percussion exam. The spring 26 acts to return the depressed piston 20 to its starting position.

The casing tube 28 and 30 covers the three pieces of the piston 20, 22, and 24 and holds the spring 26 in place. The casing tube 28 and 30 is made from two pieces of stainless steel rod which are both first drilled through to accommodate the piston 20. Then, a recess is created in each rod by milling down the center of each rod and leaving a lip on the end of each piece so that once attached together, the spring 26 and piston 20 will be secured inside the casing 28 and 30 via this ledge. To attach the two pieces of the casing 28 and 30 to one another, one piece is turned down a small amount and threaded while the other piece is bored out a small amount and tapped. These two rods join at this threaded joint. In addition, the outer edge of the casing 30 is threaded to mate with the tapper base 12.

As mentioned above, the piston assembly 19 is made from three pieces 20, 22, and 24. The finger pad piece 24 is made of stainless steel by turning down a stainless steel rod on the lathe to create a flat surface for the finger to press followed by a shaft. The last few millimeters of the shaft are further turned down and then threaded to create the joint between the finger pad piece 24 and the main piston body 20.

The main piston body 20 is made from brass. Brass is used because it has self-lubricating properties while still maintaining an appreciable density (as opposed to Teflon). The main piston body 20 is made by first drilling and tapping either end of a brass rod in order to create a mating threaded hole for the finger pad 24 and piston head 22. Then either end of the brass rod is turned down on the lathe to a diameter which will fit through the holes created in the casing tube.

The piston head piece 22 is made from stainless steel rod which is turned down on a lathe. The head itself is made round and smooth because it will come into contact with the patient. The shaft is further turned down and threaded at the last few millimeters in order to mate the shaft of the piston head 22 to the threaded hole in the piston body piece 20 described above.

The spring 26 is a stainless steel compression spring without modification.

The hammer-action assembly 14 is formed by aligning the piston body 20 into the top half 28 of the casing piece. Then the spring 26 is slid over the bottom portion of the piston body 20 and is compressed as the bottom half 30 of the casing is mated to the top half 28 and securely screwed together. Next, the finger pad 24 and piston head 22 are mated to the threaded holes of the piston body 20 which are protruding out of the casing pieces.

The hammer-action assembly 14 can then be screwed into place on the tapper base piece 12 by mating the threaded portion of the bottom half of the casing 30 to the threaded hole of the base piece 12. Finally, the stainless steel set-screw 18 can be pressed into the holes in the tails of the base piece 12.

Figure 3:
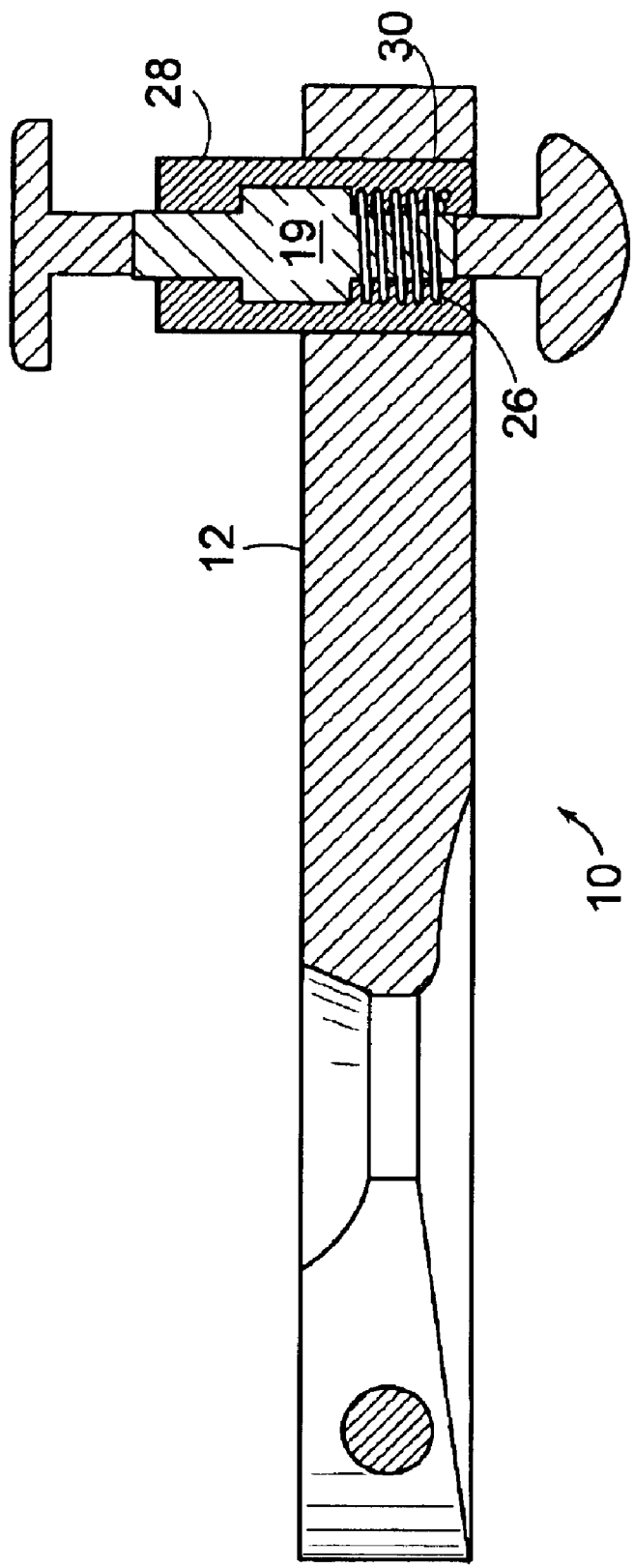
FIG. 3 is a cross-sectional view of an alternative embodiment of the medical percussion device.

Referring now to FIG. 3, there is shown an alternative embodiment of the percussion device 10 with pieces made from a die-casting or from a plastic injection molding process, so that the part count may be reduced from eight to four total pieces. In this embodiment, the base piece 12, upper casing 28, and lower casing 30 may all be combined into two symmetrically split pieces, of which one is shown in FIG. 3, which meet and are assembled around the piston 19. The piston 19 may be formed from a single piece (reducing it from 3 pieces to 1 piece). In this design, the spring 26 is first positioned on the piston 19. Then the piston 19 and spring 26 are placed in one half of the combined base-casing part. Finally, the other symmetrical base-casing part is mated to the identical half and the two are sealed together with a bonding material. The stainless steel set-screw 18 is pushed into the holes at the tails of the base 12 as described above. If the base-casing combined part is made from plastic, the set-screw may not be necessary as the plastic may be flexible enough to allow for a tight fit without a set-screw.

Figure 4A:
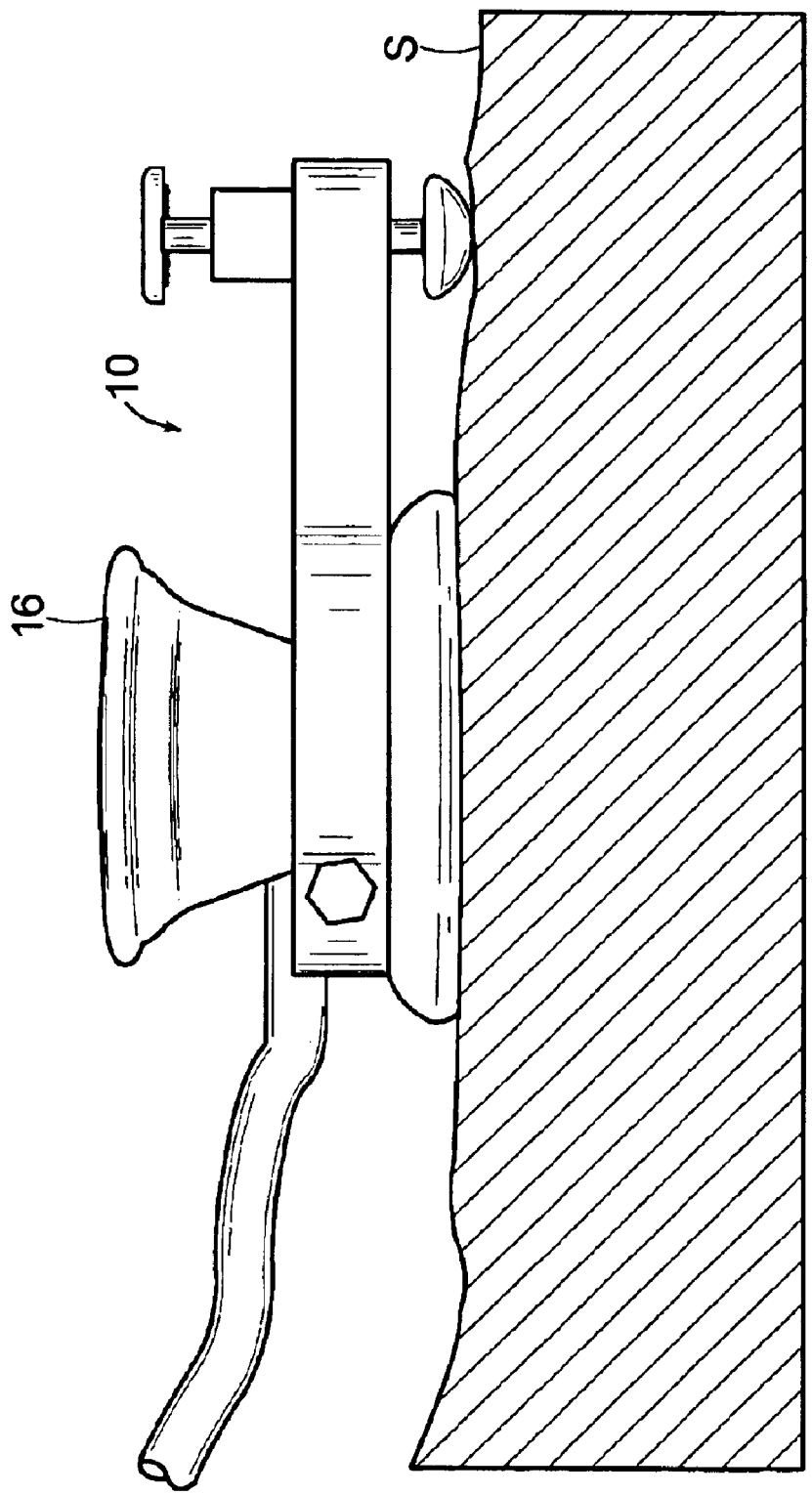
FIGS. 4A and 4B illustrate a sequence of steps for using the medical percussion device in accordance with the invention.
Figure 4B:
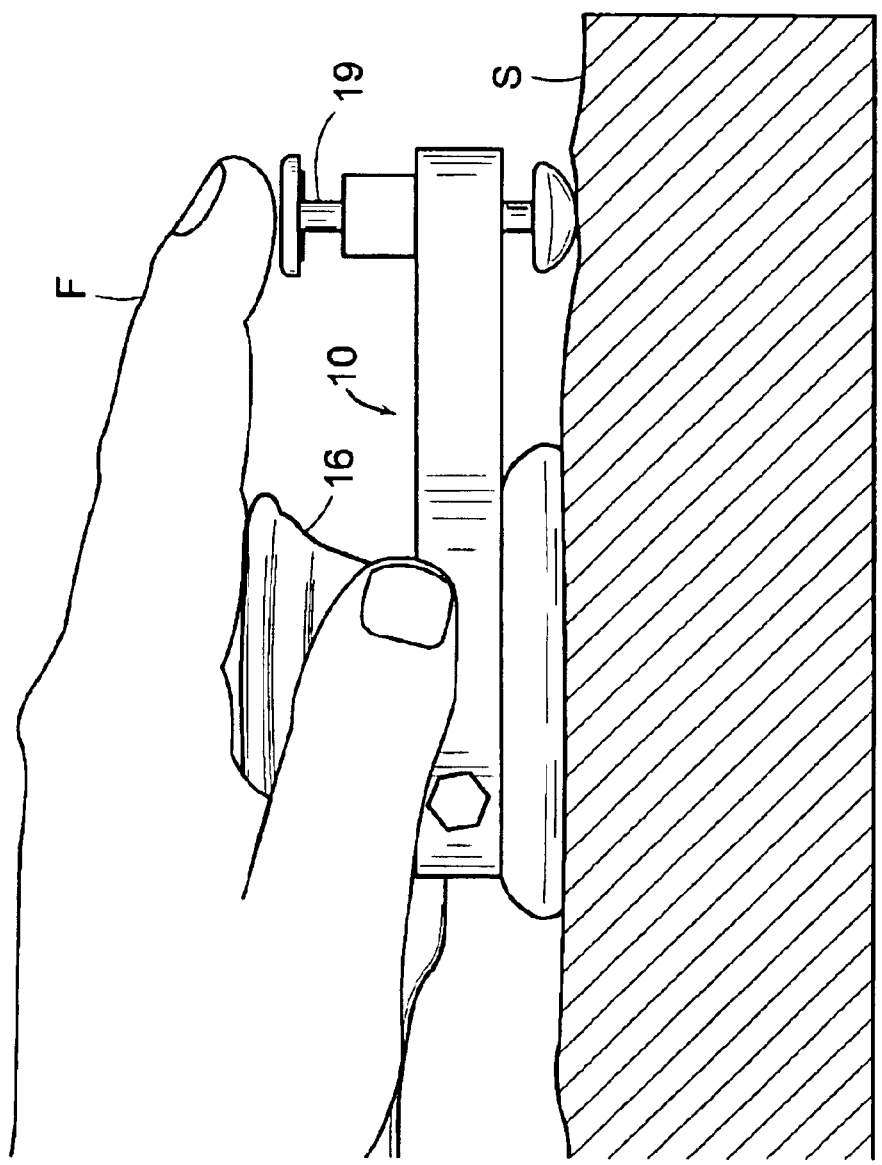

In use, as illustrated in FIGS. 4A and 4B, the mechanical percussion device 10 attaches to the head of the stethoscope 16 and is designed to be used in conjunction with the stethoscope. While the healthcare professional is listening to the thorax or abdomen with the stethoscope, the percussion device 10 may be used by depressing the spring-loaded piston 19 with the index finger, F (FIG. 4B), of the same hand that holds the stethoscope head 16 against the patient's skin, S. The resonant sounds of the body cavity will be distinctly audible through the stethoscope earpieces. The topologic pattern of percussion and comparative percussion techniques described in clinical medicine texts such as "Bates' Guide to Physical Examination and History Taking, 8th edition," by Lynn S. Bickley and Peter G. Szilagyi, Lippincott Williams & Wilkins, Philadelphia, 2003, the entire contents of which are incorporated herein by reference, may still be followed with the percussion device 10. The piston may be repeatedly depressed and released to created a consistent and regular tapping action that will aid in diagnoses.

While this invention has been particularly shown and described with references to preferred embodiments thereof, it will be understood by those skilled in the art that various changes in form and details may be made therein without departing from the scope of the invention encompassed by the appended claims. For instance, the shape and feel of the device can be different than that described above. Any suitable material can be used to make the various parts of the percussion device. The hammer action can implement different types of mechanical mechanisms, such as, tube bearing, weighted pivot, rolling weight, and bow action snap-back mechanisms. Other types of designs for different finger motions for the mechanical action are contemplated, as well, such as, for example, angled piston motion, rolling motion, or a camera trigger motion with a button on the edge of the device rather than on the back of the device. Moreover, an electronic or electromagnetic actuator can be used in place of the manual device.

What is claimed is:

1. A medical percussion device comprising:
    a base adapted to be clipped to the head of a stethoscope with a hammer support extending therefrom; and
    a hammer supported by the hammer support and actuated by a user to tap on the patient while the stethoscope head is adjacent to the skin of the patient.

2. The device of claim 1, wherein the hammer includes a finger pad that is depressed by the user to actuate the hammer.

3. The device of claim 2, wherein the hammer includes a flared piston head piece that taps on the patient when the user depresses the finger pad.

4. The device of claim 3, wherein the finger pad and piston head piece are made from stainless steel.

5. The device of claim 1, further comprising a casing supported by the hammer support, the hammer having a main piston body being positioned in the casing.

6. The device of claim 5, wherein the casing is made from stainless steel.

7. The device of claim 5, wherein the main piston body is made from brass.

8. The device of claim 5, further comprising a spring positioned around at least a portion of the main piston body and within the casing, the spring acting to return the hammer to its starting position after being actuated by the user.

9. The device of claim 8, wherein the spring is a stainless steel compression spring.

10. The device of claim 1, further comprising a set-screw used to secure the base to the head of the stethoscope.

11. A medical percussion device comprising:
    a base adapted to be clipped to the head of a stethoscope with a hammer support extending over a patient;
    a casing supported by the hammer support;
    a hammer including a finger pad, a flared piston head piece, and a main piston body, the piston body being positioned within the casing, the finger pad being depressed by a user to actuate the hammer to cause the head piece to tap on the patient; and
    a spring positioned around at least a portion of the main piston body and within the casing, the spring acting to return the hammer to its starting position after the hammer is actuated by the user.

12. A medical percussion device comprising:
    a means to be clipped to the head of a stethoscope with a support extending therefrom; and
    a means mounted to the support and actuated by a user to tap on the patient while the stethoscope head is adjacent to the skin of the patient.

13. A method of aiding the percussion portion of a physical exam of a patient comprising:
    clipping a base with a hammer support to the head of a stethoscope, while extending the hammer support therefrom; and
    actuating a hammer supported by the hammer support to tap on the patient while the stethoscope head is adjacent to the skin of the patient.

14. The method of claim 13, wherein the actuating includes depressing a finger pad of the hammer.

15. The method of claim 14, wherein the depressing causes a head piece of the hammer to tap on the patient.

16. The method of claim 13, further comprising returning the hammer to its starting position after the actuating.

17. A stethoscope comprising:
    a stethoscope head;
    a base clipped to the stethoscope head with a hammer support extending therefrom; and
    a hammer supported by the hammer support and actuated by a user to tap on the patient while the stethoscope head is adjacent to the skin of the patient.

* * * * *